US006638431B2

(12) United States Patent  (10) Patent No.: US 6,638,431 B2
Back et al.                (45) Date of Patent:     Oct. 28, 2003

(54) FORMULATION AND METHOD FOR TREATING WETTED SURFACE ELEMENTS IN CLIMATE CONTROL SYSTEMS

(75) Inventors: Dwight D. Back, Pembroke Pines, FL (US); Robert P. Scaringe, Rockledge, FL (US); John A. Meyer, Palm Bay, FL (US)

(73) Assignee: Mainstream Engineering Corporation, Rockledge, FL (US)

( * ) Notice: Subject to any disclaimer, the term of this patent is extended or adjusted under 35 U.S.C. 154(b) by 72 days.

(21) Appl. No.: 09/847,402

(22) Filed: May 3, 2001

(65) Prior Publication Data

US 2002/0162800 A1 Nov. 7, 2002

(51) Int. Cl.$^7$ ................................................ B01D 33/00
(52) U.S. Cl. ................ 210/698; 252/181; 423/DIG. 14; 424/618; 424/638; 424/641; 424/646; 424/650; 510/199; 514/493; 514/494; 514/495; 514/499
(58) Field of Search ................... 252/181; 423/DIG. 14; 510/199; 514/495, 499, 493, 494; 210/698; 424/618, 638, 641, 646

(56) References Cited

U.S. PATENT DOCUMENTS

| 3,329,607 | A | * | 7/1967  | Colobert et al. ........ 252/181 X |
| 3,699,052 | A | * | 10/1972 | Petrey, Jr. et al. ...... 252/181 X |
| 4,164,477 | A | * | 8/1979  | Whitley |
| 4,332,791 | A | * | 6/1982  | Raaf et al. ..................... 424/52 |
| 4,335,116 | A | * | 6/1982  | Howard |
| 4,725,427 | A | * | 2/1988  | Ashmead et al. ........ 514/494 X |
| 4,885,156 | A | * | 12/1989 | Kotilainen et al. ........... 424/54 |
| 5,104,644 | A | * | 4/1992  | Douglas ...................... 424/53 |
| 5,149,354 | A | * | 9/1992  | Delaney ................. 514/495 X |
| 5,302,292 | A | * | 4/1994  | Soeder et al. ........... 252/181 X |
| 5,405,620 | A | * | 4/1995  | Beres et al. ................. 424/638 |
| 5,762,821 | A | * | 6/1998  | Tate ........................ 252/181 X |
| 5,942,480 | A | * | 8/1999  | Prevost et al. .......... 510/199 X |
| 6,139,879 | A | * | 10/2000 | Taylor .................... 514/499 X |
| 6,387,415 | B1 | * | 5/2002  | Garris ........................ 424/618 |

* cited by examiner

*Primary Examiner*—Richard D. Lovering
(74) *Attorney, Agent, or Firm*—Crowell & Moring LLP

(57) ABSTRACT

A formulation and method to treat and control microbial growth present in the water of climate control systems such as air conditioner air handlers, dehumidifiers, and humidifiers, which formulation can be entrained and dispersed into to living space air. Specifically, a formulation is provided in the form of a tablet or a spray for being applied onto a wetted surface element present in these systems which will effectively control the growth of microbes such as fungus, molds, bacteria, and virus present on the surface for an extended period of time. The formulations include at least two metals, at least two chelating agents, at least one surfactant, and at least one viscosity enhancing compound.

29 Claims, 2 Drawing Sheets

Figure 1:
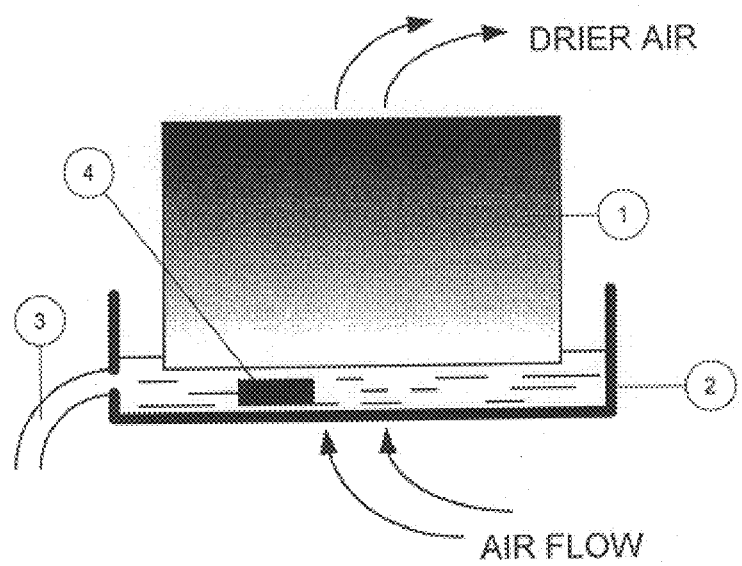
Figure 2:
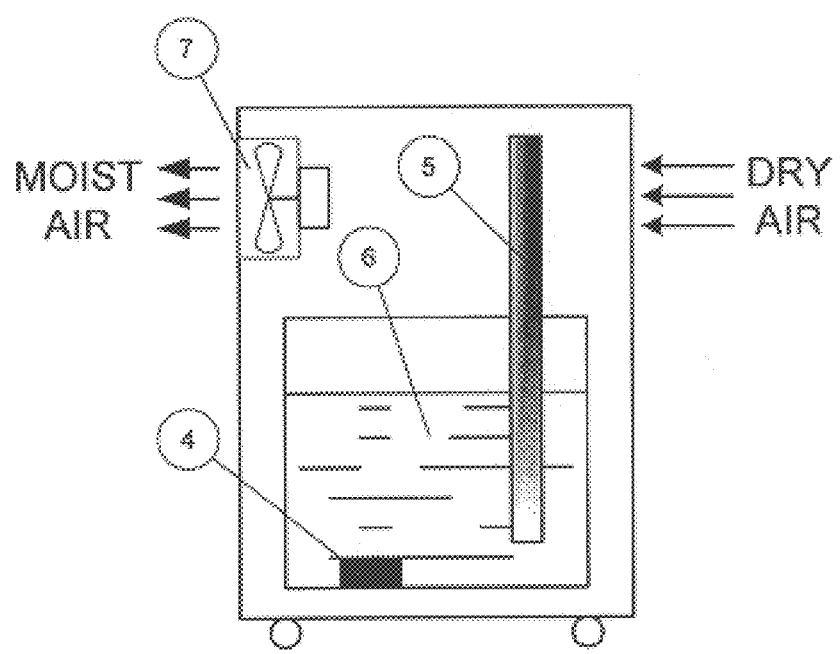

FORMULATION AND METHOD FOR TREATING WETTED SURFACE ELEMENTS IN CLIMATE CONTROL SYSTEMS

BACKGROUND OF THE INVENTION

The present invention relates to a formulation and method for treating wetted surface elements in climate control systems and more particularly, to an improved treatment method and product which arranges long-term effectiveness in climate control systems.

Air-conditioners, heat pumps, dehumidifiers, and humidifiers, can collectively be called climate control systems. All of these systems possess a wetted surface element ("WSE") by which or through which air passes. Air-conditioners, heat pumps, and dehumidifiers circulate air by a cooled surface. As the warm air is cooled below its dewpoint, water condenses and accumulates on the cooled surface and typically falls into a collection reservoir where eventually the collected water drains to the outdoors via a drain line. On the wet and cool condensing surface and the collection reservoir, conditions are favorable for the growth of microbes which can be entrained by the passing air. Depending on the operation or duty cycle of the particular system, this condensed water sometimes remains stagnant for long time periods, thereby promoting microbial and fungal growths on water-contacted parts and surfaces.

During winter months, humidifiers are sometimes used to humidify dry air by passing the dry air across a wetted surface. Systems such as pan humidifiers, portable humidifiers, power wetted-element humidifiers, atomizing humidifiers, ultrasonic humidifiers, and rigid media humidifiers are widely used. A humidifier by nature requires a water source and an associated wetted surface which is evaporated into drier air. These water sources can promote microbial and fungal colony growths that could be entrained into the ventilation system via the passing air flow. Treating the water used in these systems with biocides can dramatically reduce the likelihood that airborne toxins are entrained.

The dispersion of microbes such as bacteria, virus, mold, and fungus can be the source of sickness to exposed occupants in the climate controlled area. For example, *Legionella pneumophilia* has been found to exist in such an environment and has been linked to Legionnaire's disease. Other microbes can contribute to "sick home" or "sick building" syndrome. Many people are also allergic to the molds and fungus entrained in the dwelling's ventilation as the air passes over contaminated water.

Treating the source of these microbes reduces or eliminates the amount of microbes entrained by passing air microbes. As these microbes can persist on the WSE as well as the water reservoir, treatment of the WSE is critical because it can serve as a continuous source of microbes for the water reservoir. Hence, treatment of the WSE should be performed at a minimum, and a coordinated treatment of the WSE and water reservoir would be optimum. The treatment of the WSE and water reservoir can be performed in one step if compounds having suitable dissolution properties are chosen and the treatment of the condensing water or wetted surface provides for drain off of the treatment compounds to the water reservoir. After treating the WSE and the water reservoir with biocidal compounds, a slow dissolution tablet such as that described in U.S. patent application Ser. No. 09/520,006, now U.S. Pat. No. 6,303,039, should deter any further microbial growth in the water reservoir.

Metals including silver (Ag), nickel (Ni), zinc (Zn), copper (Cu), and tin (Sn) are known in the art as effective biocides. For example, Ag is effective against virus and bacteria. In particular, a concentration of about 0.02 ppm (or 20 ppb) in water is effective against *Legionella pneumophilia*. Cu is also an effective algaecide and in some cases a bactericide. Other metals can also be effective against different microbes to differing degrees.

Metals such as these can be used as a biocide in water soluble, insoluble or slightly soluble forms. The choice depends on the particular application involving the biocide. For example, the biocide formulations taught by copending U.S. patent application Ser. No. 09/520,006 filed Mar. 6, 2000, and now U.S. Pat. No. 6,303,039 are for slow dissolution metal salts to treat a water reservoir over an extended period of time, whereas other applications may require delivery of a higher concentration of biocide over a short period of time. In either case, it is critical that the biocide formulation account for the presence of other anions that will be present in the water. Hence, of critical importance in an aqueous biocidal metal application is the stability of the metal ions in solution.

There are many anions present in water with the potential to precipitate out metal ions, and because their availability in solution is necessary to be effective against the microbes, retention of the metals in solution is highly beneficial. If provisions are not made to ensure some level of these ions in solution, they will precipitate out negating their effect against microbes, and additional materials will need to be added costing the user more in raw materials and maintenance. One known technique to ensure that these effective compounds remain in solution where they are effective against microbes is through the use of chelating agents which have a stronger affinity toward the metal ions than do the anions present in the water. Certain chelating agents such as salicylic acid (SA) are also generally known by those skilled in the art to be biocides. For example, SA is known to be an effective fungicide. Hence, the use of chelating agents such as SA along with the metal biocides will provide dissolved and stable chelated metal ions as well as a dissolved, metal-free chelating agent that can also supplement the metal biocide.

Most WSE cleaning or disinfection products are sprays (aerosols or pump) which are used to flush the surface. Most of these disinfectants contain quaternary ammonium salts, chlorine dioxide, alcohols, ethers, or trichloroethylene. A surface flush or wash generally removes debris and certain microbes physically and serves as a short-lived biocide.

SUMMARY OF THE INVENTION

An object of the present invention is to provide a biocide spray solution containing effectively chelated biocide metals which can be applied to a WSE present in a climate control device surface to treat and then control the growth of microbes on the surface over an extended period of time.

Another object of the present invention is to provide a formulation of metal salts and chelating agents combined with viscous water-soluble compounds such as polyhydric alcohols and polymers which can be applied as a spray to produce a residue of the viscous compound with the metal salts and chelating agents dissolved or dispersed therein when some or all of the water has evaporated from the solution sprayed onto a WSE in a climate control device.

These objects have been achieved by a product in the form of a cleaning and disinfection solution to the WSE that has a two-fold effect: first, it flushes and cleans the surface "shocking" the microbes with biocides, and, second, a long-term effect which will provide a maintenance level of biocide which eliminates any re-growth of the microbes on the surface. The latter, as we have recognized, is possible because glycerol (a polyhydric alcohol), water-soluble polymers, or other viscosity enhancing compounds are soluble in water and can be used to increase the viscosity or "stickiness" of the solution. Compounds such as polymers, glycerol or other polyhydric alcohols generally have a much higher boiling point than water so if the water evaporates, remaining residue will contain dissolved or dispersed biocide salts and chelating agents. Then, as more water condenses or flows through or across the surface, the dispersed or dissolved biocide metals and chelating agents will dissolve providing disinfection to the WSE and ultimately the drain pan or water reservoir collecting excess water. The extended time for which the present invention provides for treating a WSE is thus derived from the presence of water soluble residue remaining after the surface was sprayed. The slow dissolution of these ingredients will also eventually drain off of the WSE into a water reservoir or pan, and then through the drain line. Thus, this type of spray treatment would also provide for disinfection of the reservoir or pan and drain lines over an extended period of time.

The method comprising the present invention is to combine two or more metals, one or more chelating agents, and one or more surfactants in a single formulation so that the combination potentially produces synergistic effects with regard to microbe efficacy. These synergisms can exist with multiple metals, for example, because microbes colonies typically grow and thrive synergistically. Hence, by using one or more metals in solution, it is possible to produce an unexpected efficacious biocide product which exceeds the capabilities of using only one metal biocide at the maximum concentration allowed according to EPA drinking water standards.

BRIEF DESCRIPTION OF THE DRAWINGS

Other objects, advantages and novel features of the present invention will become apparent from the following detailed description when considered in conjunction with the accompanying drawings herein.

FIG. 1 is a schematic view of an evaporator with wetted surface element (WSE) with which the present invention is used;

FIG. 2 is a schematic view of a notable humidifier with wetted surface element with which the present invention is used.

DETAILED DESCRIPTION OF THE DRAWINGS

According to a currently preferred embodiment of the present invention, a water solution having active agents, comprised of at least two metals and at least two chelating compounds, is sprayed onto a WSE in a climate control device. The WSE can be an evaporator as shown in FIG. 1, cold plate or the like at a temperature below the dew point of the humid air passing through or by the surface. The WSE could also be a pad, mesh or other water retentive or high surface area substrate. Examples of specific devices which may include a WSE are a dehumidifier, a humidifier as shown in FIG. 2 and an air-conditioning system.

In FIG. 2, the portable humidifier has a wetted surface element (WSE) 5. The formulation in the form of a tablet 4 can be placed in the water reservoir 6. Alternatively, the WSE 5 can be sprayed with the formulation to disinfect the element as air is forced over and through the WSE 5 by the fan 7.

FIG. 1 is a schematic of typical cooling surface 1 by which humid air passes generating a condensate in pan 2 which drains by line 3. A biocide tablet or the like 4 can be placed in the pan to provide long term disinfection of water in reservoir 2. The wetted surface element 1 is sprayed with the formulation of this invention to disinfect the surface and to also provide a residue which will dissolve and provide longer-term treatment of surface 1 and the water and element in reservoir 2.

A water treatment formulation of the present invention can be formed by dissolving metal salts and chelating agents in a solution of water and a viscosity enhancing compound. Viscosity enhancing compounds include, but are not limited to, polymers and polyhydric alcohols. One polyhydric alcohol which is inexpensive and useful is glycerol. Metal salts which can dissolve in the water solution include copper sulfate, zinc sulfate, copper acetate, copper chloride, copper nitrate, silver nitrate, silver sulfate, silver phosphate, silver fluoride, silver acetate, nickel nitrate, nickel sulfate, zinc acetate, zinc chloride, zinc gluconate, zinc nitrate, zinc salicylate, zinc sulfate, and tin sulfate.

Water soluble chelating agents include water soluble salts of an aminopolycarboxylic coumpound or sodium and potassium conjugate base salts of weak acid chelating agents such as citric acid (CA), salicylic acid (SA), ethylenediaminetetraacetic acid (EDTA), nitrilotriacetic acid (NTA), and diethylenetriamine pentaacetic acid (DTPA). In addition, surfactants may be added to enhance the cleaning ability, spreadability or other chemical properties. One currently preferred surfactant is sodium or potassium dodecyl sulfate, although other water soluble anionic, cationic, or nonionic surfactants are contemplated as being usable in this invention.

The biocide metal and chelating agents may also be provided as a water soluble complex salt rather than individual components in combination with, or instead of, the individual soluble metal salts and chelating agents.

It is also a currently preferred embodiment of the present invention to use a combination of two or more metals with one or more chelating agents in the formulation. Because metals have differing biocidal effectiveness against bacteria, virus, fungi, and algae, it is therefore advantageous to use a combination which will provide a broad scope of biocidal activity. In addition, it is advantageous to use two or more chelating agents because different metals have different solution equilibrium constants with the chelating agents and by providing two or more chelating agents, we can better maximize the solution concentration of all metal ions. Furthermore, microbes sometimes co-exist synergistically so that a combination of metals may act synergistically against microbe colonies and can be more effective than a single metal.

EXAMPLES FOR BIOCIDE SPRAY TABLET

Example 1

A formulation of 24% glycerol, 73% water, 1% sodium citrate dihydrate, 1% disodium ethylenediaminetetraacetic acid (EDTA), and 1% copper sulfate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. The resulting plate growth of colonies was found to be Too Numerous To Count (TNTC). As a comparison, a control containing 1 part purified water and 9 parts contaminated water was prepared and analyzed in the same fashion gave similar results: TNTC.

Example 2

A formulation of 48% glycerol, 48% water, 1% sodium citrate dihydrate, 1% disodium ethylenediaminetetraacetic acid (EDTA), 1% potassium lauryl sulfate and 1% copper sulfate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. No growth or colonies were observed in this plate sample. As a comparison, a control containing 1 part purified water and 9 parts contaminated water was prepared and analyzed in the same fashion yielded a colony and growth count that was TNTC.

Example 3

A formulation of 48.5% glycerol, 48.5% water, 1% sodium citrate dihydrate, 1% disodium ethylenediaminetetraacetic acid (EDTA), 1% copper sulfate and 0.1% silver nitrate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. A few Large colonies were observed (<20) in this plate sample. As a comparison, a control containing 1 part purified water and 9 parts contaminated water was prepared and analyzed in the same fashion yielded a colony and growth count that was TNTC.

Example 4

A formulation of 48% glycerol, 48% water, 1% sodium citrate dihydrate, 1% disodium ethylenediaminetetraacetic acid (EDTA), 1% TritonX 200 (sodium alkylarylpolyether sulfonate) surfactant and 1% copper sulfate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. The resulting plate growth of colonies was found to be Too Numerous To Count (TNTC). As a comparison, a control containing 1 part purified water and 9 parts contaminated water was prepared and analyzed in the same fashion gave similar results: TNTC.

Example 5

A formulation of 48% glycerol, 48% water, 1.0% sodium citrate dihydrate, 1% disodium ethylenediaminetetraacetic acid (EDTA), 1% TritonX 405 (octylphenoxypolyethoxyethanol, water and polyethylene glycol) surfactant and 1% copper sulfate was mixed into solution. After this time, 1 mL of sample was removed and combined with standard plate growth medium, put into a petri dish and allowed to incubate for 48 hours. After this time, 1 mL of sample was removed and combined with standard plate growth medium and allowed to incubate for 48 hours. The resulting plate growth of colonies was found to be Too Numerous To Count (TNTC). As a comparison, a control containing 1 part purified water and 9 parts contaminated water was prepared and analyzed in the same fashion gave similar results: TNTC

Example 6

A formulation of 48% glycerol, 48% water, 1% sodium citrate dihydrate, 1% disodium ethylenediaminetetraacetic acid (EDTA), 1% TritonX 100 (octylphenoxypolyethoxyethanol, polyethylene glycol) surfactant and 1% copper sulfate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. The resulting plate growth of colonies was found to be Too Numerous To Count (TNTC). As a comparison, a control containing 1 part purified water and 9 parts contaminated water was prepared and analyzed in the same fashion gave similar results.

Example 7

A formulation of 48% glycerol, 48% water, 1% sodium citrate dihydrate, 1% disodium ethylenediaminetetraacetic acid (EDTA), 1% potassium lauryl sulfate and 1% copper sulfate was mixed into a solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 8

A formulation of 48.2% glycerol, 48.2% water, 1% sodium citrate dihydrate, 1% disodium ethylenediaminetetraacetic acid (EDTA), 0.7% potassium lauryl sulfate and 1% copper sulfate was mixed into a solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 9

A formulation of 48.3% glycerol, 48.3% water, 1% sodium citrate dihydrate, 1% disodium ethylenediaminetetraacetic acid (EDTA), 0.4% potassium lauryl sulfate and 1% copper sulfate was mixed into a solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. Several large colonies (>20) were observed in this sample. As a comparison, a control containing 1 part purified water and 9 parts contaminated water was prepared and analyzed in the same fashion yielded a colony and the growth count that was TNTC.

Example 10

A formulation of 48.4% glycerol, 48.4% water, 1% sodium citrate dihydrate, 1% disodium ethylenediaminetetraacetic acid (EDTA), 0.2% potassium lauryl sulfate and 1% copper sulfate was mixed into a solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. Several large colonies (>20) were observed in this sample. As a comparison, a control containing 1 part purified water and 9 parts contaminated water was prepared and analyzed in the same fashion yielded a colony and the growth count that was TNTC.

Example 11

A formulation of 69.4% water, 23% glycerin, 1% sodium citrate dihydrate, 1% disodium ethylene diamine tetraacetate (EDTA), 4.6% sodium dodecyl sulfate (70% purity), and 1% copper sulfate was mixed into solution. After this time, 1 mL of sample was removed and combined with standard plate growth medium, put into a petri dish and allowed to incubate for 48 hours. After this time, 1 mL of sample was removed and combined with standard plate growth medium and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 12

A formulation of 69.4% water, 23% glycerin, 1% sodium citrate dihydrate, 1% disodium ethylene diamine tetraacetate (EDTA), 4.6% sodium dodecyl sulfate (70%), 1% copper sulfate, and 0.09% silver sulfate was mixed into solution. The mixture was combined with water contaminated with bacteria present in cooling systems in a 1 part solution to 9 parts contaminated water and allowed to sit for 24 hours. After this time, 1 mL of sample was removed and combined with standard plate growth medium, put into a petri dish and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 13

A formulation of 69% water, 23% glycerin, 1% sodium citrate dihydrate, 1% disodium ethylene diamine tetraacetate (EDTA), 4.6% sodium dodecyl sulfate (70%), 1% copper sulfate, 0.09% silver sulfate and 1% zinc sulfate was mixed into solution. After this time, 1 mL of sample was removed and combined with standard plate growth medium, put into a petri dish and allowed to incubate for 48 hours. After this time, 1 mL of sample was removed and combined with standard plate growth medium and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 14

A formulation of 69% water, 23% glycerin, 1% sodium citrate dihydrate, 1% disodium ethylene diamine tetraacetate (EDTA), 4.6% sodium dodecyl sulfate (70%), 1% copper sulfate, 1% zinc sulfate and 0.0046% silver sulfate was mixed into solution. After this time, 1 mL of sample was removed and combined with standard plate growth medium, put into a petri dish and allowed to incubate for 48 hours. After this time, 1 mL of sample was removed and combined with standard plate growth medium and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

Example 15

A formulation of 97% water, 0.5% glycerin, 0.06% sodium citrate dihydrate, 0.03% disodium ethylene diamine tetraacetate (EDTA), 2.4% sodium dodecyl sulfate (70%), 0.1% copper sulfate, 0.02% zinc sulfate and 0.0007% silver sulfate was mixed into solution. After this time, 1 mL of sample was removed and combined with standard plate growth medium, put into a petri dish and allowed to incubate for 48 hours. After this time, 1 mL of sample was removed and combined with standard plate growth medium and allowed to incubate for 48 hours. No growth or colonies were observed in this sample. As a comparison, a control containing 1 part purified water and 9 parts contaminated water was prepared and analyzed in the same fashion yielded a colony and the growth count that was TNTC.

While the invention has been described in connection with currently preferred embodiments, procedures, and examples, it is to be understood that such detailed description is not intended to limit the invention to the described embodiments, procedures, and examples. Instead, it is the intent of the present invention to cover all alternatives, modifications, and equivalent which may be included within the spirit and scope of the invention as defined by the claims hereto.

What is claimed is:

1. A composition for treating a wetted surface element in a climate control system, comprising at least two biocide metals, at least two chelating agents, at least one surfactant, and at least one viscosity enhancing compound, wherein the at least two chelating agents are selected from the group consisting of water soluble salts of citric acid (CA), salicylic acid (SA), ethylene diaminetetraacetic acid (EDTA), nitrilotriacetic acid (NTA), and diethylenetriamine pentaacetic acid (DTPA).

2. The composition of claim 1, wherein the at least two chelating agents are water soluble salts of an aminopolycarboxylic compound.

3. The composition of claim 1, wherein the at least two chelating agents are supplied as a biocide metal salt.

4. The composition of claim 1, wherein at least one of the at least two biocide metals is supplied as a salt of a chelating agent.

5. The composition of claim 1, wherein the at least one surfactant is selected from the group consisting of sodium dodecyl sulfate and potassium dodecyl sulfate.

6. The composition of claim 1, wherein the at least one viscosity enhancing compound is selected from the group consisting of polymers and polyhydric alcohols.

7. The composition of claim 6, wherein the polyhydric alcohol is glycerol.

8. The composition of claim 1, wherein the at least two biocide metals are selected from the group consisting of Ag, Cu, Ni, Sn and Zn.

9. The composition of claim 8, wherein the Ag is in a soluble form selected from the group consisting of silver nitrate, silver phosphate, silver sulfate, silver fluoride, and silver acetate.

10. The composition of claim 8, wherein the Cu is a soluble form selected from the group consisting of copper sulfate, copper acetate, copper chloride, and copper nitrate.

11. The composition of claim 8, wherein the Ni is a soluble form selected from the group consisting of nickel sulfate and nickel nitrate.

12. The composition of claim 8, wherein the Zn is a soluble form selected from the group consisting of zinc sulfate, zinc acetate, zinc chloride, zinc gluconate, zinc nitrate, zinc salicylate, and zinc sulfate.

13. The composition of claim 8, wherein the Sn is a soluble tin sulfate.

14. A method for treating a wetted surface element a climate control system, comprising applying a formulation of claim 1 onto condensing water in the system or the wetted surface element.

15. A method for treating a wetted surface element in a climate control system, comprising at least two biocide metals each of which has a concentration of not more than 1% by weight, at least two chelating agents, at least one surfactant, and at least one viscosity enhancing compound.

16. The composition of claim 15, wherein the at least two chelating agents are water soluble salts of an aminopolycarboxylic compound.

17. The composition of claim 15, wherein the at least two chelating agents are supplied as a biocide metal salt.

18. The composition of claim 15, wherein at least one of the at least two biocide metals is supplied as a salt of a chelating agent.

19. The composition of claim 15, wherein the at least one surfactant is selected from the group consisting of sodium dodecyl sulfate and potassium dodecyl sulfate.

20. The composition of claim 15, wherein the at least one viscosity enhancing compound is selected from the group consisting of polymers and polyhydric alcohols.

21. The composition of claim 20, wherein the polyhydric alcohol is glycerol.

22. The composition of claim 15, wherein the at least two biocide metals are selected from the group consisting of Ag, Cu, Ni, Sn and Zn.

23. The composition of claim 22, wherein the Ag is in a soluble form selected from the group consisting of silver nitrate, silver phosphate, silver sulfate, silver fluoride, and silver acetate.

24. The composition of claim 22, wherein the Cu is a soluble form selected from the group consisting of copper sulfate, copper acetate, copper chloride, and copper nitrate.

25. The composition of claim 22, wherein the Ni is a soluble form selected from the group consisting of nickel sulfate and nickel nitrate.

26. The composition of claim 22, wherein the Zn is a soluble form selected from the group consisting of zinc sulfate, zinc acetate, zinc chloride, zinc gluconate, zinc nitrate, zinc salicylate, and zinc sulfate.

27. The composition of claim 22, wherein the Sn is a soluble tin sulfate.

28. A method for treating a wetted surface element in a climate control system, comprising applying a formulation of claim 15 onto condensing water in the system or the wetted surface element.

29. A composition for treating a wetted surface element in a climate control system, comprising a biocidal copper salt at a concentration of not more than 1% by weight, at least two chelating agents, at least one surfactant, and at least one viscosity enhancing compound, wherein the at least two chelating agents are selected from the group consisting of water soluble salts of citric acid (CA), salicylic acid (SA), ethylenediaminetetraacetic acid (EDTA), nitrilotriacetic acid (NTA), and diethylenetriamine pentaacetic acid (DTPA).

* * * * *